US005554855A

United States Patent [19]
Ueno

[11] Patent Number: 5,554,855
[45] Date of Patent: Sep. 10, 1996

[54] PHOTOPOLYMERIZATION REACTOR AND SMALL-SIZED LIGHT IRRADIATOR FOR DENTAL USE

[75] Inventor: Masato Ueno, Hiroshima, Japan

[73] Assignees: Molten Corporation; Chugoku Shiken Kabushiki Kaisha, both of Hiroshima, Japan

[21] Appl. No.: 96,305

[22] Filed: Jul. 26, 1993

[30] Foreign Application Priority Data

Jul. 31, 1992 [JP] Japan .............................. 4-059422 U
Aug. 7, 1992 [JP] Japan .............................. 4-061473 U
Mar. 12, 1993 [JP] Japan .............................. 5-017019 U
May 31, 1993 [JP] Japan .................................. 5-154429

[51] Int. Cl.$^6$ ............................ A61C 19/00; A61C 13/14
[52] U.S. Cl. ................... 250/455.11; 250/504 R; 250/504 H
[58] Field of Search ................... 250/455.11, 504 H, 250/504 R

[56] References Cited

U.S. PATENT DOCUMENTS 1,472,779 11/1923 Anderson ....................... 250/504 H
1,952,306 3/1934 Bird ................................. 250/504 H
3,826,014 7/1974 Helding ........................... 250/504 R
4,939,374 7/1990 Greutert ......................... 250/504 R

*Primary Examiner*—Jack I. Berman
*Attorney, Agent, or Firm*—Armstrong, Westerman, Hattori, McLeland, & Naughton

[57] ABSTRACT

A photopolymerization for dental use composed of a light of sources emitting at least visible light and infrared light transparent cells charged with coolant disposed to the emission side of said light source, whereby absorb infrared light; and a board for mounting a formed article which is composed of materials for a pattern made of photopolymerizable resin, impinging the light thereon from the light source after transmitting through said cells, wherein the tranparent cell is composed of disc-like shaped main body having a hollow space therein which is formed integrally with heat resistant glass; and two glass pipes for circulation of coolant which is disposed to the cell main body communicated to the hollow space.

8 Claims, 12 Drawing Sheets

PHOTOPOLYMERIZATION REACTOR AND SMALL-SIZED LIGHT IRRADIATOR FOR DENTAL USE

BACKGROUND OF THE INVENTION

The present invention relates to a photopolymerization reactor for dental use in order to polymerize and cure photopolymerizable (or photocurable) resins used for patterning material such as a clasp, a bar, an inlay, a hard resin for facing crown in the field of a dental artificer, more particularly to a photopolymerization reactor for dental use wherein the improvements lie in a cooling mechanism.

Further, the present invention relates to a small-sized light irradiation for dental use which is used for curing composite resin or curing the inlay within the mouth.

Recently, when a clasp, a bar, a pattern for crown-bridge occlusion plane or the like is made, there is a tendency of using a photopolymerizable resin material instead of wax. Before polymerizing, the photopolymerizable material having plasticity is formed to have a predetermined shape, then polymerized and cured by irradiating it using visible or ultraviolet lights. Thus a light source emitting visible or ultraviolet lights, such as a halogen lamp is used. The conventional photopolymerization reactor using such a lamp is available. The halogen lamp is suitable for emitting light or ultraviolet rays as a photopolymerization reactor. However, infrared lights are emitted excessively, hence, there arises such a problem that the lamp and a formed article made of photopolymerizable resin are heated to an abnormally high temperature.

Particularly, when the formed article is heated to an abnormally high temperature, there arises such problems that the formed article is deformed before polymerization, a gas bubble is generated by boiling the liquid contained in the resin, such as a monomer. When the pre-attaching crown is formed, lights irradiated after the metal formed article is covered with photopolymerizable resin. The metal part is heated to a high temperature. Accordingly, when the following step is performed, it takes too much time to cool it after taking it out by using forceps. It is very inefficient work. Further, there is some probability of generating a strain in the boundary between the metal part and the resin part due to a heat expansion of the metal part.

Particularly, when the crown-bridge is formed, the occlusion plane of teeth to be supported are formed by means of photopolymerizable resin and cured, then the side faces of the teeth model are covered with wax so as to be shaped. Therefore, the occlusion plane of a pontic part is formed and cured by means of photopolymerizable resin. On using wax, there arises a problem wherein temperature rises due to light irradiation so as to melt and deform the wax.

As is often the case with the conventional device, air within the device is formed by using an exhaust fan so as to create an air flow in the light irradiation chamber. Thereby, the formed article is cooled. Such a conventional construction performe low coming efficiency since some air flows within the light irradiation chamber and into contact with the formed article. According to such a construction, abnormally heating the formed article cannot be prevented.

The present invention is made to resolve the above-mentioned problems, and the object of the present invention is to provide a construction to make it possible to maximize the cooling effect of the formed article.

In dental curing, it is known that a method for curing the photopolymerizing resin, such as composite resins, which is charged in the dental caries, by using irradiation. In such a curing, a small-sized light irradiator has hitherto been used, and known (for example Japanese Examined Utility Model Publication No. 36491/ 1990).

In many cases, a halogen lamp is used as a light source of the light irradiator. The halogen lamp outputs visible light, the amount of which is too much to be suitable for the light source of the light irradiation. However, infrared lights are excessively emitted so as to heat the lamps and neighborhood thereof too much. Conventionally, a filter for the infrared lights is disposed in the side of the light source and an exhaust fan is disposed in the back side of the light source so that the lamp and the whole device are cooled using the air cooling method. However, such a construction is insufficient for cooling. Therefore, such a halogen lamp to perform practically a cooling effect at low power can be used. It is impossible to cure an inlay in the mouth by photopolymerizing. Further, lights emitted from the halogen lamp includes ultraviolet rays so that there arises a problem of suffering due to direct irradiation to the structure of the mouth.

Accordingly, the present invention is made in view of the above circumstances. The present invention realizes a small-sized light irradiator which has a large output to polymerize and cure the conventional composit and the inlay.

SUMMARY OF THE INVENTION

In accordance with the present invention, there is provided a photopolymerization reactor for dental use comprising:

(a) a light source emitting at least visible light and infrared light;

(b) transparent cells charged with a coolant disposed to the emission side of said light source, to absorb infrared light; and (c) a board for mounting a formed article which is composed of materials for a pattern made of photopolymerizable resin, impinging the light thereon from said light source after transmitting through said transparent cells.

It is preferable that said transparent cells are composed of disc-like shaped cell main bodies having a hollow space therein which is formed integrally with heat resistant glass; and two glass pipes for circulation of the coolant which is disposed in said cell main body to communicate with said hollow space.

The light irradiation is undergone to the formed article mounted on the board for mounting. In the light emitted from the light source, infrared light is absorbed on passing through the tranparent cell. In the light irradiation chamber, the lights, from which the infrared light is removed, are irradiated so as to polymerize and cure without heating the photopolymerizable material.

In accordance with the present invention, there is also provided a small-sized irradiator for dental use comprising:

(a) a light source emitting visible, infrared and ultraviolet light provided with a substantially half ball-shaped reflector which converges at least visible light of said visible, infrared and ultraviolet light to a predetermined direction;

(b) a transparent cell transmissive to visible light disposed on the emission side of said light source and which absorbs infrared and ultraviolet light;

(c) a light guide to impinge lights passing through said transparent cell from one side end, and emit from the other side end which is directed in a predetermined direction; and (d) a casing with a handle enclosing said light source and transparent cell, provided with said light guide to its end; wherein said transparent cell has a hollow space therein, and said hollow space is charged with fluid.

It is preferable that said transparent cell is composed of a disc-like shaped cell main body having a hollow space therein and two fine tubes for fluid circulation fixed to said cell main body to communicate with said hollow space, wherein said conical shaped cell is disposed such that a bottom portion of said conical shaped cell is faced to a side of one side end of said light guide.

In the light incident to the visible light transparent cell emitted from the light source, most of the infrared and ultraviolet lights are removed and lights composed of visible lights advance. The light incident to the light guide advances from the tip thereof.

DETAILED DESCRIPTION

Figure 1:
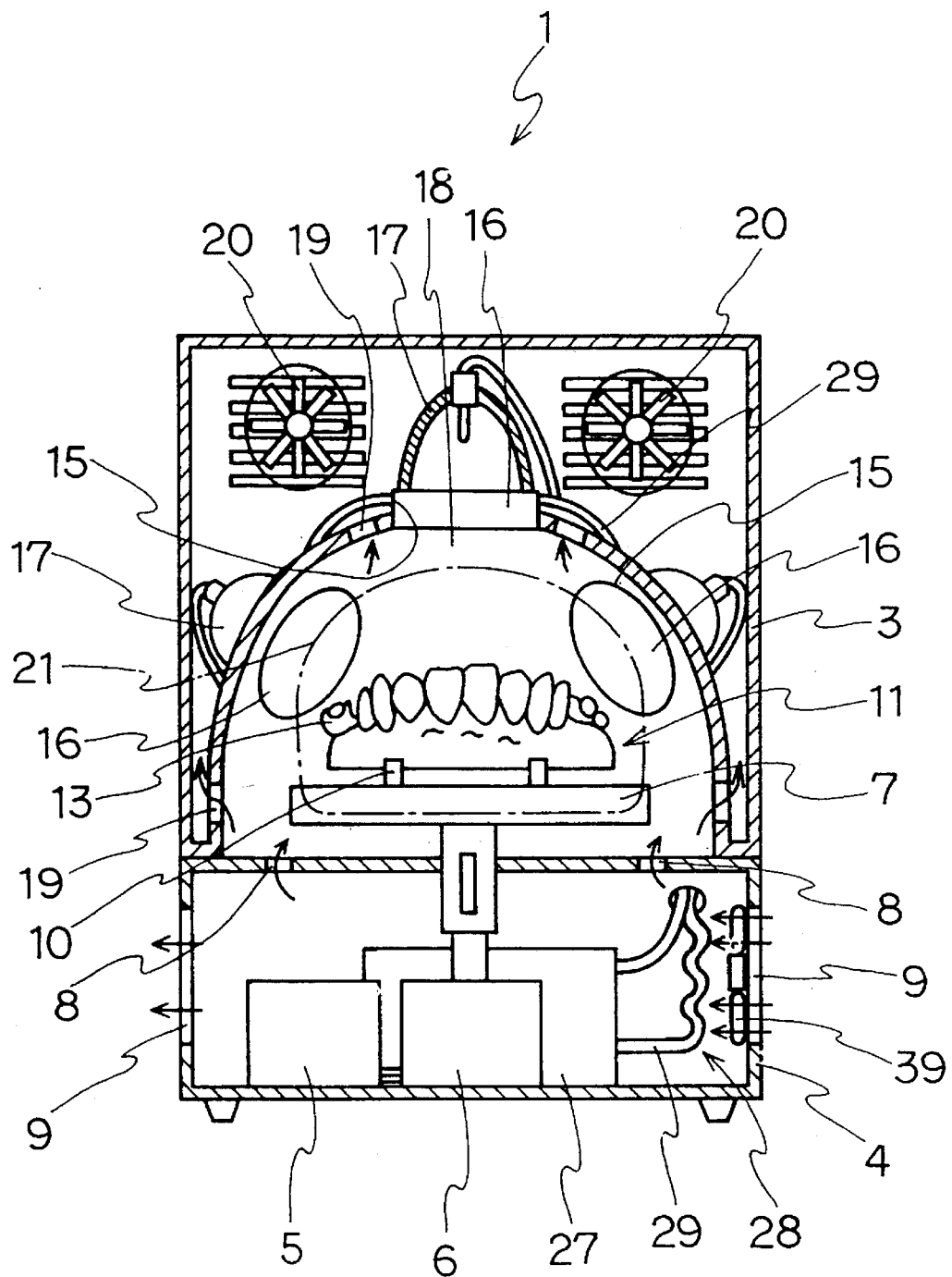
FIG. 1 is a cross-sectional view showing an embodiment of the present invention.
Figure 2:
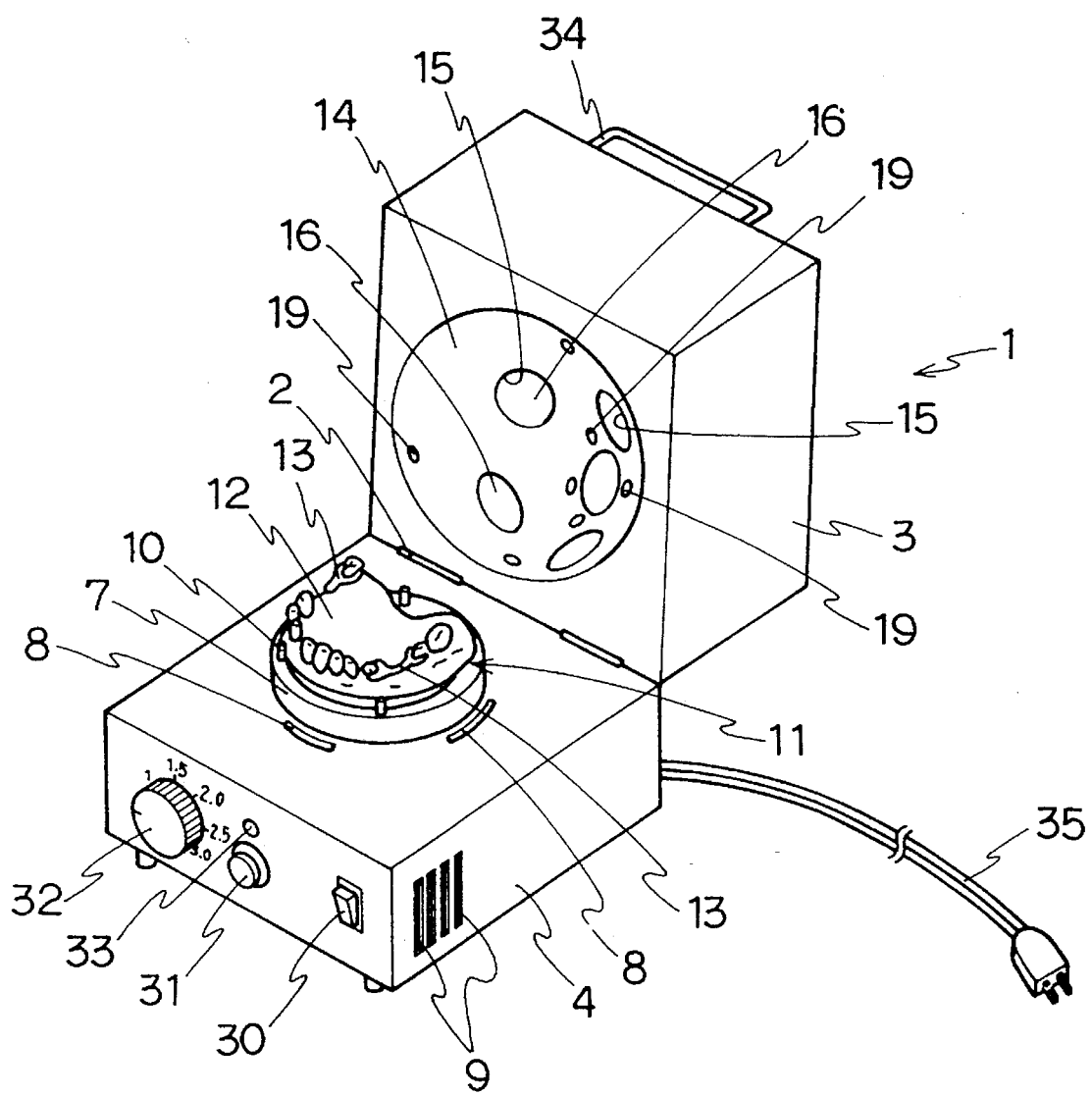
FIG. 2 is a perspective view of FIG. 1 when it is opened.

FIGS. 1 and 2 show a photopolymerization reactor 1 for dental use consisting of an upper casing 3 and a lower casing 4 connected by hinge 2, making the photopolymerization reactor capable of opening and closing.

Power transformer 5 and motor 6 and the like are enclosed in the lower casing 4 and a disc-like-shaped board for mounting, for example, a turntable 7 is disposed on the upper surface of the lower casing 4. Numeral 8 indicates holes for air supply, and air introduced from slits 9 on the right side of the side surface of the lower casing 4 is introduced through the holes 8. The turntable is provided with a plurality of guide-pins 10, 10, . . . adjacent marginal edges of the turntable 7, whereby the portions of formed article 11 mounted on the table 7 could be defined. Formed article 11 is composed of jaw pattern (or model) 12 made of gypsum and material for the pattern made of photopolymerizable resin 13 which is mounted thereon in the predetermined position and shape.

Numeral 14 indicates a substantially half-ball shaped reflector which is mounted on the upper casing 4 and subjected to a surface treatment so as to be a mirror on the inner surface. Five holes 15 are totally formed on a top part and neighborhood of the reflector 14. Numeral 16 indicates tranparent cells charged with coolant, for example water, ethylene glycol and so on and placed on the holes 15, numeral 17, 17 . . . indicate a plurality of lamps which are disposed so as to adequately irradiate the transparent cells 16, 16 . . . . Light sources 17, for example, emit visible, ultraviolet or infrared rays with halogen lamp. As a light source, xenon lamp, metal halide lamp and the like can be used other than the halogen lamp. A space for irradiating room 18 is defined by reflector 14, tranparent cells 16 and the upper surface of lower casing 4. A mirror-surface can be defined by the upper-side of the lower casing 4.

Each halogen lamp 17 is placed outside of the light-irradiating room 18. Vacuum evaporation is subjected to the inner surface of the reflectors 14 of these lamps 17 in order to permeate only infrared light and to reflect other kinds of lights. Numeral 19 indicates holes for air evacuation which are placed on surrounding area of the central halogen lamp 17 and lower area of the reflector 14. Numeral 20 indicates fans for air evacuation to evacuate air from the holes 19 out of the instrument. These fans 20 drive depending on the ON-OFF action of "main switch" described afterwards.

Driving these fans 20 introduces air from slits 9 on the lower casing 4, further the air enters light-irradiating room 18 through holes for air supply 8, goes out of the light-irradiating room 18 through holes for air evacuation 19 and is evacuated outside of the instrument after cooling the lamps 17 and so on. Numeral 27 indicates a pump enclosed in the lower casing 4, which is connected with a tube 29 to transparent cells 16. A fan 39 for air supply introduces air from slits 9 on the right side of the figure of lower casing 4. On an adjacent area to the fan 39, the tube 29 is folded to construct heat exchanger 28. In other words, coolant inside of the tube 29 is cooled in heat exchanger 28 by the air introduced from the fan 39.

On the center of light-irradiating room 18, lights emitted from five halogen lamps 17 are converged, whereby a region 21 is formed to which converge reflecting lights from reflector 14. If material for the pattern made of photopolymerizable resin 13 is placed on said region, the resin would be irradiated most efficiently, therefore photopolymerization proceeds quickly. This region 21 is named specified region.

Figure 3:
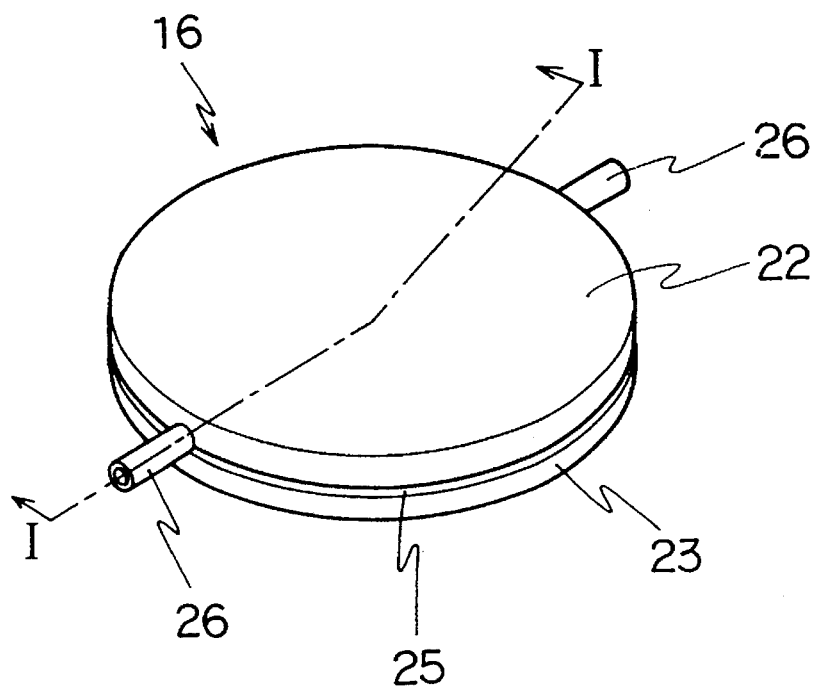
FIG. 3 is a perspective view showing an embodiment of the tranparent cell of the present invention.
Figure 4:
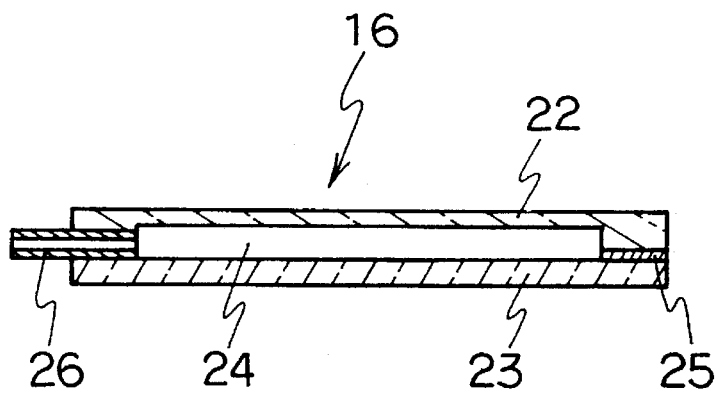
FIG. 4 is a cross-sectional view taken along with a line I—I in FIG. 3.

As shown in FIGS. 3 and 4, a transparent cell 16 is constructed such that two pieces of transparent glass plates 22, 23 are secured in a manner as to be spaced at about 3 mm. A space 24 defined by the glass plates 22, 23 is charged with coolant. The two pieces of glass plates 22, 23 are bonded with adhesive 25 so that the space 24 can be sealed. Numeral 26, 26 designates a fine tube for communicating with the space 24. The space is charged with coolant by the one fine tube 26 and discharged by another fine tube 26. The cell 16 can be made by not only heat resistant glass but also heat resistant synthetic resin. The cell 16 can be formed into a concave lens or a convex lens by changing a thickness thereof.

Figure 5:
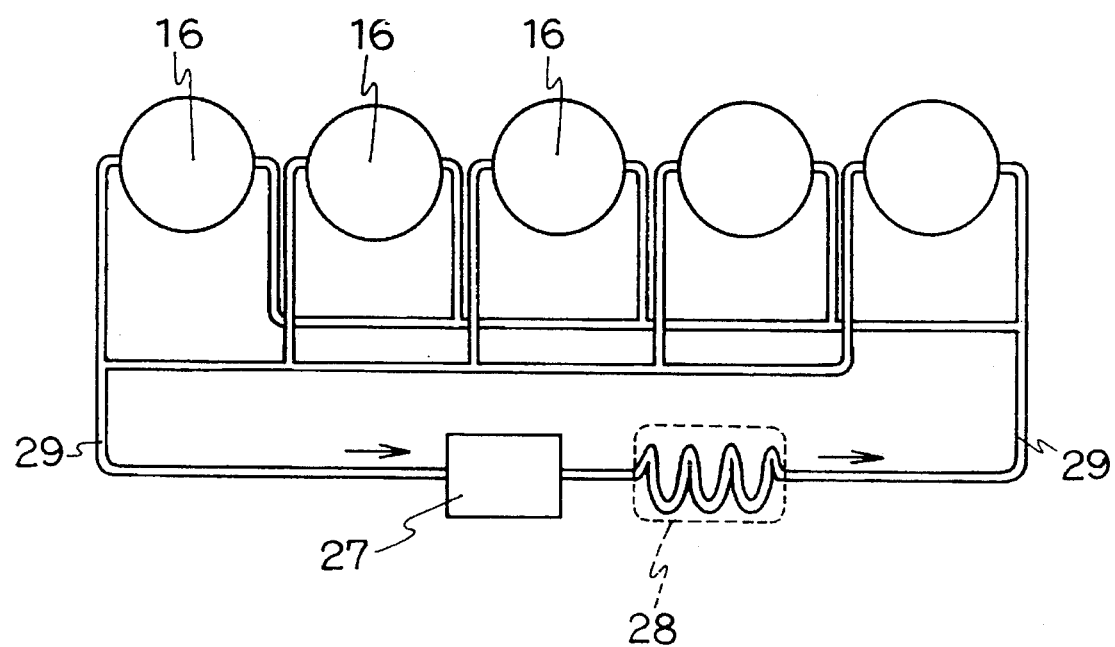
FIG. 5 is a schematic view showing arrangement of the tranparent cells of FIG. 3 and circulating route of coolant.

The five transparent cells 16, 16 . . . are connected in parallel with a pump 27 as shown in FIG. 5. Each cell 16 is charged with coolant and the coolant is circulated by driving the pump 27. While the coolant is circulated, the coolant is cooled by a heat exchanger.

Figure 6:
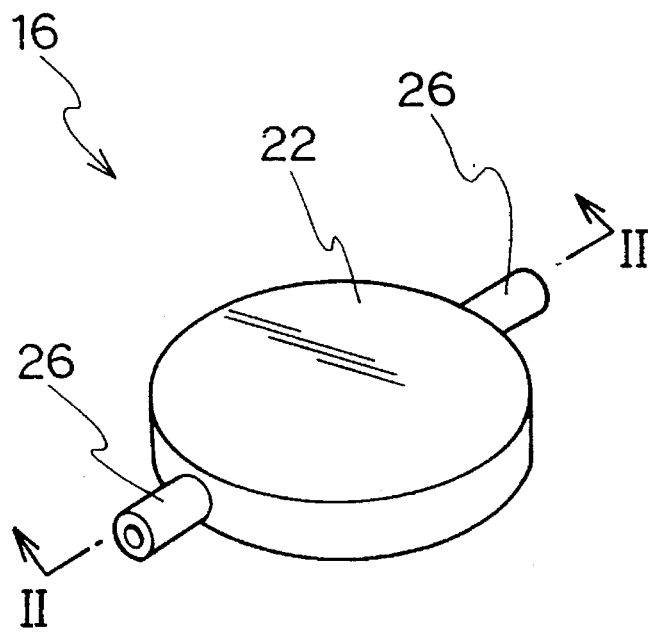
FIG. 6 is a perspective view showing another embodiment of the transparent cell of the present invention.
Figure 7:
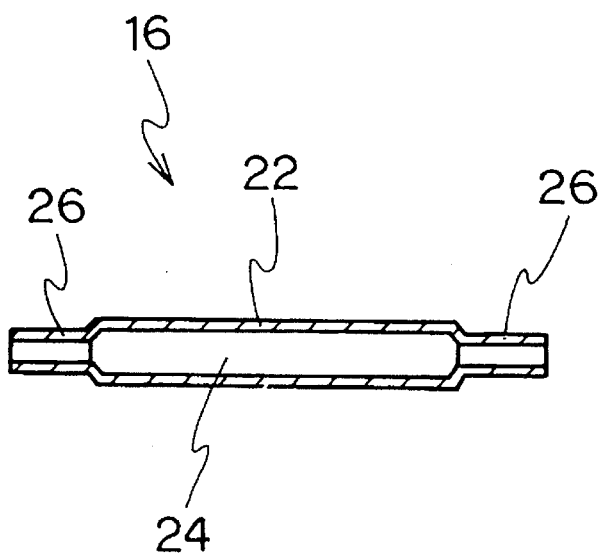
FIG. 7 is a cross-sectional view taken along with a line II—II in FIG. 6.

FIG. 6 shows another embodiment of transparent cell, the transparent cell 16 is composed of disc-like shaped cell main body 22 having hollow space 24 therein, formed integrally with heat resistant glass, for example, Pyrex (registered trademark) glass, two glass pipes 26 which are deposited radially on the lateral side surface of cell main body 22 communicate hollow space 24 thereby. These glass pipes 26 are also formed with heat resistant glass. Size of cell main body 22 can be about 5 cm in a disc diameter, about 10 mm in whole disc thickness and about 1 mm in glass thickness. Pipes 26, 26 are used for influx and drain of coolant respectively. Tranparent cell 16 can function as concave lens or convex lens to converge light onto a specified portion by changing the thickness of the upper and lower side. Transparent cells 16 are disposed adjacent to halogen lamp 17, and absorb infrared light from halogen lamp 17. It therefore results in strain occurrence by repeated heating and cooling while using for a long time, even if cooling is carried out by passing coolant through hollow space 24. Fluid leakage often happens in such structures of transparent cell 16 as being spacer interposed between two glasses or being O-ring interposed and clamped between them because of little resistance to the above-mentioned heat fluctuation. In the present device, fluid leakage is prevented by integral formation of transparent cell 16 with glass. This transparent cell 16 is also prevented from failing due to an external shock by fixation via a supporter made of rubber (not shown in the figure).

Figure 8:
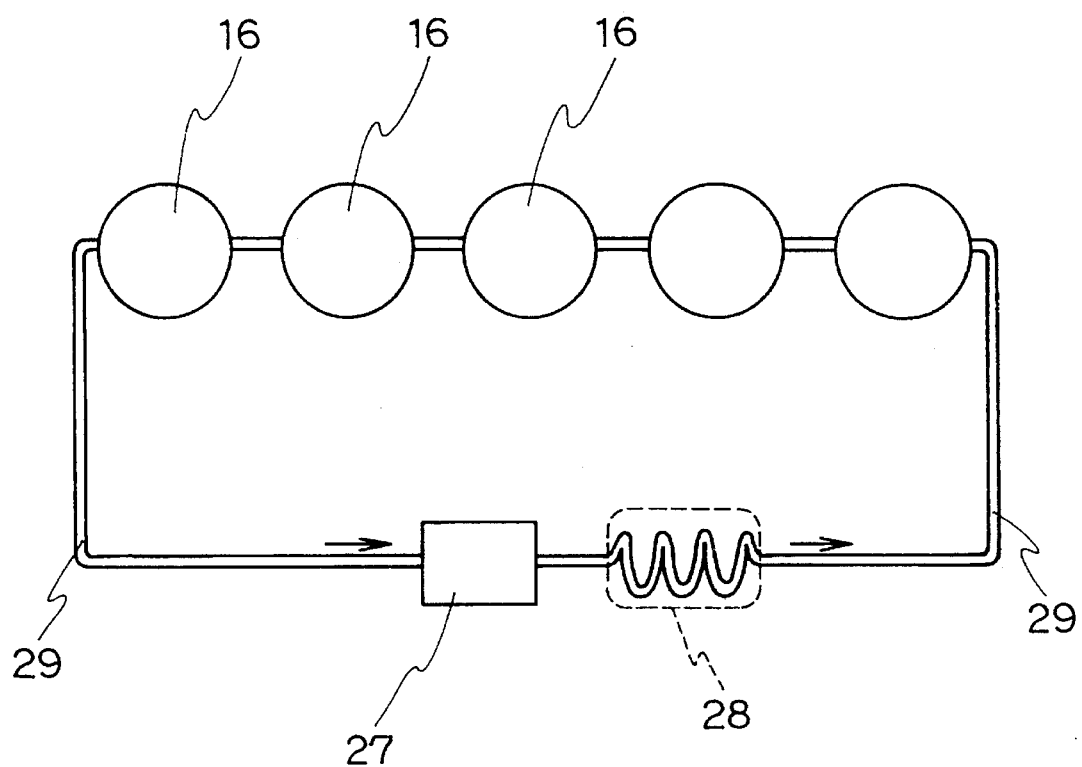
FIG. 8 is a schematic view showing arrangement of the tranparent cells of FIG. 6 and circulating route of coolant.

As shown in FIG. 8, five transparent cells 16 are connected serially to pump 27 by tube 29. Under driving of pump 27, coolant is charged and passed to each cell 16. Coolant is cooled at heat exchanger 28 while circulating. If necessary, a tank can be disposed serially to pump 27.

Back to FIG. 2, numeral 30 indicates power switch, numeral 31 indicates starting switch, numeral 32 indicates timer respectively. Changing over starting switch 31 ON under state of power switch ON, halogen lamps 17 are lighted and turntable 7 is rotated in the meantime preset by timer 32. Timer 32 can be optionally set every second depending on the configuration and volume of material for the pattern made of photopolymerizing resin 13 of formed article 11. Maximum one minute is satisfactorily used as the present time for practical use. Numeral 33 indicates lamp displaying the state of power switch 31 ON i.e. the interlocked to power switch 30 ON-OFF state. Numeral 34 indicates a handle disposed on upper surface of upper casing 3 for the purpose of opening and closing the upper casing 3. Numeral 35 indicates electronic cord. In some cases, irradiation may be carried out without rotation of turntable 7 for a predetermined time depending on material type for the pattern, so as to deal with such a case, appropriate means for making turntable stop can be disposed optionally.

Figure 9:
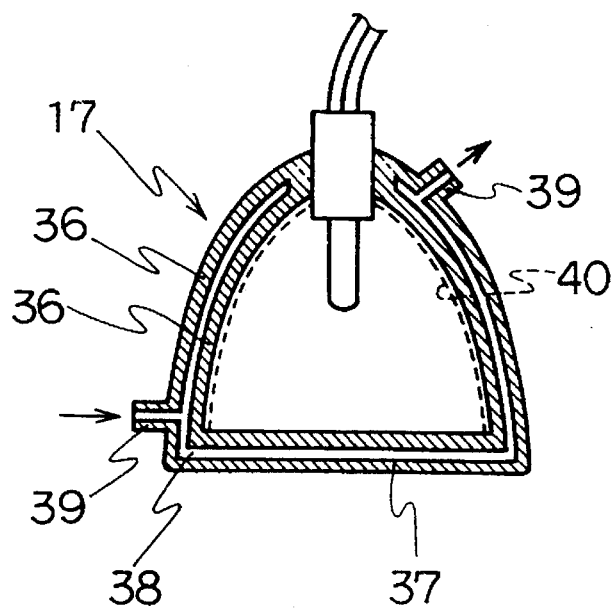
FIG. 9 is a cross-sectional view showing another embodiment of a halogen lamp of the present invention.

FIG. 9 shows another embodiment of the present invention, wherein the reflector 36 of the halogen lamp 17 has a duplex structure and the reflector 36 is integrally combined with the cell 37. The reflector 36 is formed in such a manner that the hollow space of the reflector 36 is communicated with the hollow space 38 of the cell 37. The hollow space 38 is charged or discharged with coolant via two fine tubes 39, 39 attached to the cell 37. Vacuum evaporated surface 40 is formed on the inside surface of the reflector 36 so that only the infrared lights can be passed therethrough, and the visible light and ultraviolet lights are reflected thereon.

Figure 10:
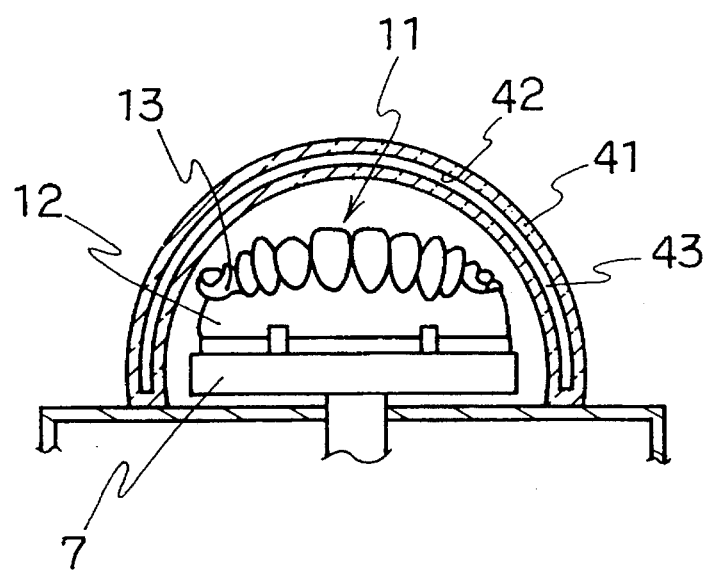
FIG. 10 is a cross-sectional view showing still another embodiment of photopolymerization reactor of the present invention.

FIG. 10 shows still other embodiment of the present invention, which is cooled by using a cell 41 enclosing a turntable 7 and a formed article 11. The cell 41 is made of a transparent heat resistant glass or heat resistant synthetic resin. The cell 41 has a hollow space 42 therein, the hollow space is charged with a coolant 43 and sealed. In the example shown in FIG. 10, coolant 43 is sealed within the cell 41. On the other hand, coolant 43 can be circulated by separately providing with a pump and a tube connected thereto.

Figure 11:
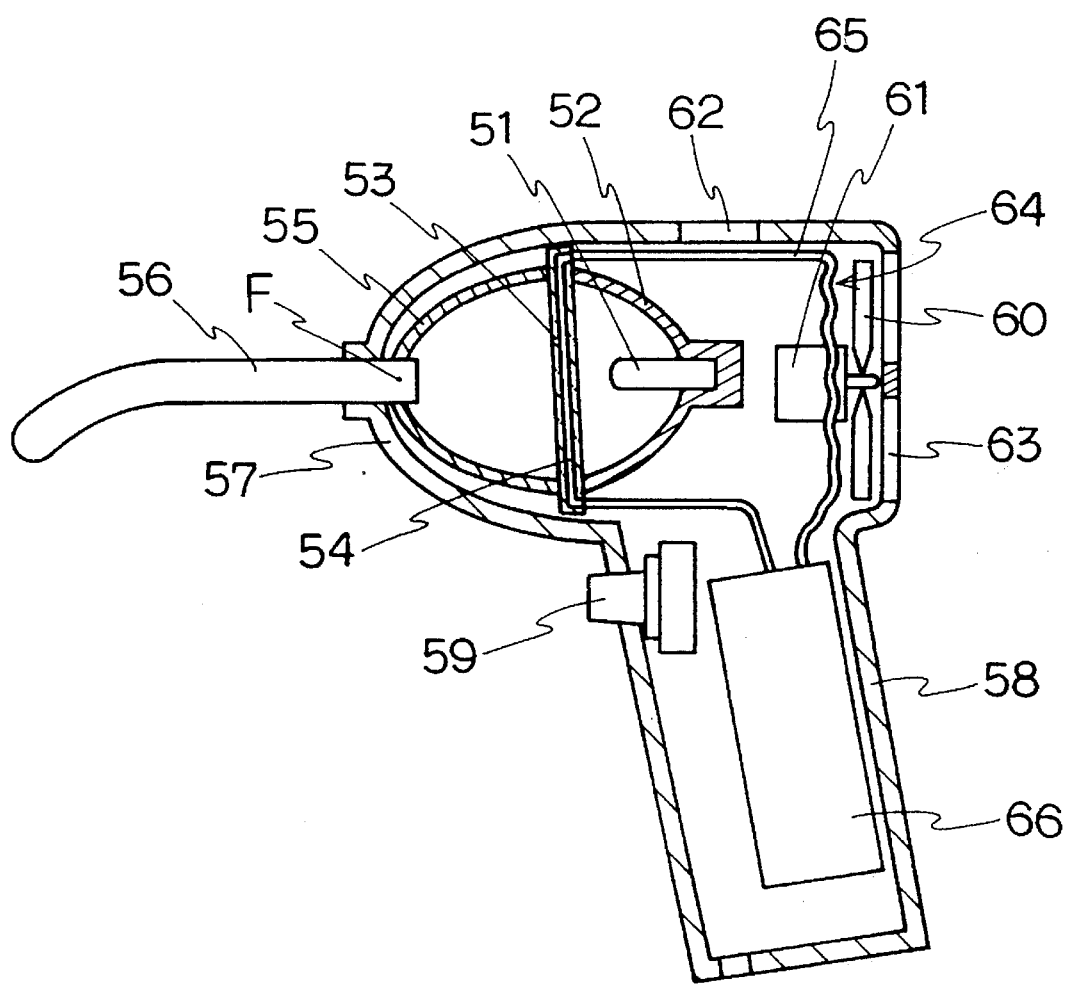
FIG. 11 is a sectional view showing one embodiment of the light irradiation of the present invention.

FIG. 11 shows a small-sized light irradiator, wherein numeral 51 indicates light source, for example, halogen lamp emitting visible, infrared and ultraviolet lights. As a light source, xenon lamp, metal halide lamp and the like can be used other than halogen lamp. Numeral 52 indicates a substantially half-ball shaped reflector which reflects visible light from said halogen lamp. Numeral 53 indicates transparent cell of visible light which is disposed in an open space of the reflector 52 i.e. the emission side of the light, with charged fluid 54 therein. This all functions as a filter of infrared light and ultraviolet light. Namely, more than about 80% of the infrared light and almost all of the ultraviolet light impinging to said cell 53 is absorbed. Numeral 55 indicates another reflector which is disposed outside of the cell 53. Water, ethylene glycol or silicone oil can be used as fluid 54.

Numeral 56 indicates light guide formed of glass fiber, the visible light which is transmitted to the cell 53 impinging from one side thereof, and further emitted from the other side end which is directed to a desired direction. Casing is rotatably provided with light guide 56, and light guide 56 is detachably inserted into the casing. Casing 57 is formed of plastics which is disposed a handle 58. Numeral 59 indicates a power switch which is equipped to the handle 58. Numeral 60 indicates disclosed fan for air exhaust, which is driven by motor 61. Driving fan supplies air from hole 62 for air supply, and further evacuates air through hole air exhaust. Adjacent to the fan 60, heat exchanger 64 is subjected to blowing air from folded tube 65. Tube 65 is communicated between cell and a pump 66. This pump 66 can be of the construction having a tank for water storage therein (not shown in the figure). With such a construction, fluid 54 charged in the cell 53 is circulated by the pump 66, and cooled at heat exchanger 64. Namely, heated fluid 54 by absorbance of infrared light at the cell 53 is cooled at heat exchanger 64, and again supplied to cell 53. Motor 61 can change its ON-OFF State by operation of power switch 59. Lamp 51, motor 61, pump 66 and power switch 59 are connected by an electronic code which is not shown in the Figure. One motor can be used both as motor 61 and motor for driving of pumps 66. Tubing at the heat exchanger 64 is preferably formed with metal pipe which is superior to heat conductivity such as copper pipe, and at the other portion of tubing elastic silicone tube can be used.

Figure 12:
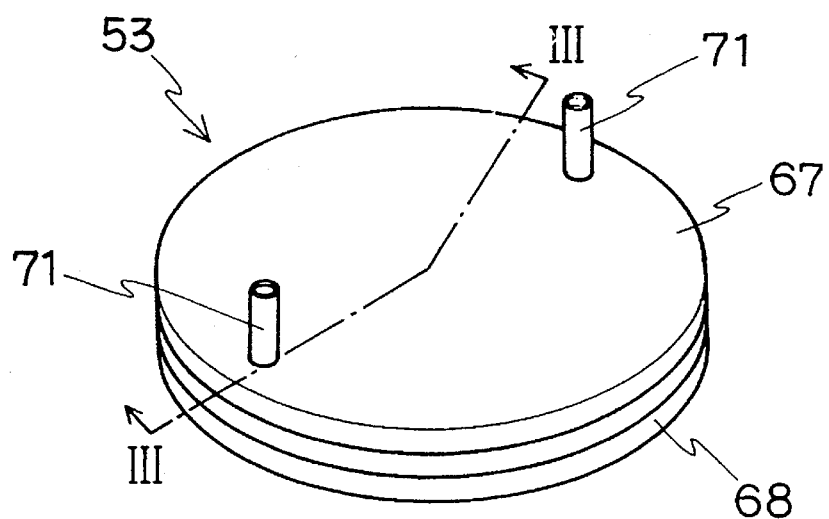
FIG. 12 is a perspective view showing a transparent cell attached to the light irradiator of FIG. 11.
Figure 13:
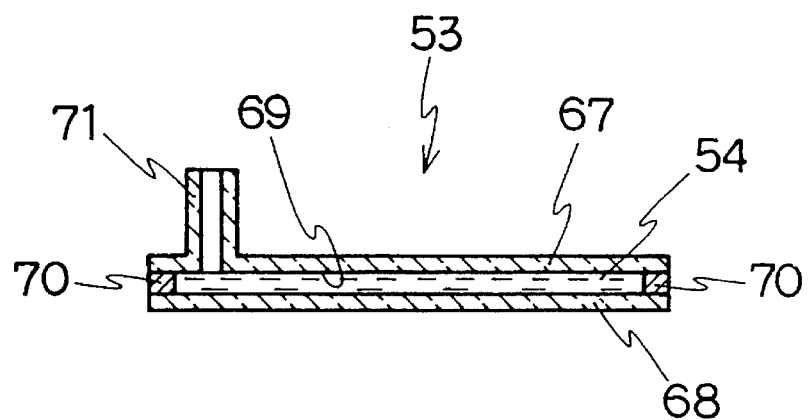
FIG. 13 is a sectional view taken along with a line III—III in FIG. 12.

As shown in FIGS. 12 and 13, transparent cell is composed of two transparent glasses 67, 68 which are spaced with a space 69 in 3 mm thickness between them, and fluid 54 is charged to the space 69. Two glasses 67, 68 can be spaced with adhesive 70, to seal space 69. Numeral 71 indicates fine tubes with which communicating space 69, and one of them are used as supply and the other as drain of water. This transparent cell 53 can be composed of heat resistant plastic or heat resistant glass. Two glasses 67, 68 of transparent cell 53 can be also be constructed to concave lens by changing their thickness adequately. Emission light from lamp 51 concave to the spot F, which is inside of the light guide 56 directly, or by reflection at reflector 52 and by further transmission through transparent cell 53.

Figure 14:
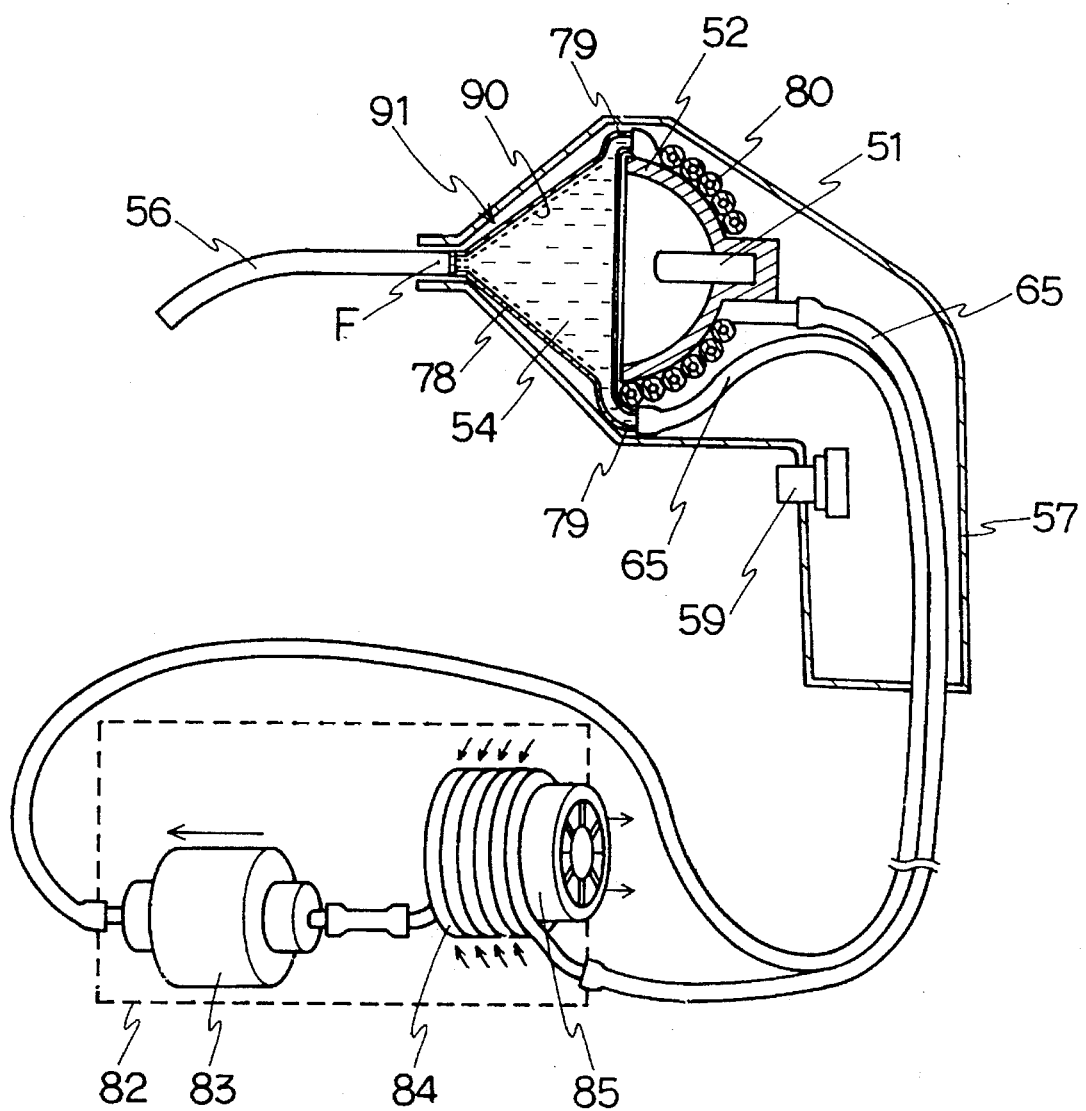
FIG. 14 is a sectional view showing another embodiment of the present invention.

FIG. 14 shows another embodiment of the present invention comprising an integrally formed cone-shaped cell main body 78 having vacant space therein by heat resistant glass and two fine tubes 79, 79 for fluid circulation which are communicated with said vacant space thereby fixed to said cell main body 78. In a vacant space of inside of the cell body 78, aforementioned fluid 54 is charged, inner surface of the vacant space of cell main body 78 is provided with mirror 90 to reflect light.

The down-side of the cone of cell main body 78, faces open end of reflector 52, and the top of the cone faces one edge of light guide 56. The light emitted from light source 51 therefore impinges on transparent cell 91, limited almost of infrared light and ultraviolet light by fluid 54 therein, converges to spot F inside of light guide 56 while reflecting to mirror 90, and further is introduced by light guide 56. Light impringed to light guide 56 which comprises visible light mainly, is emitted from another side of the guide.

Figure 15:
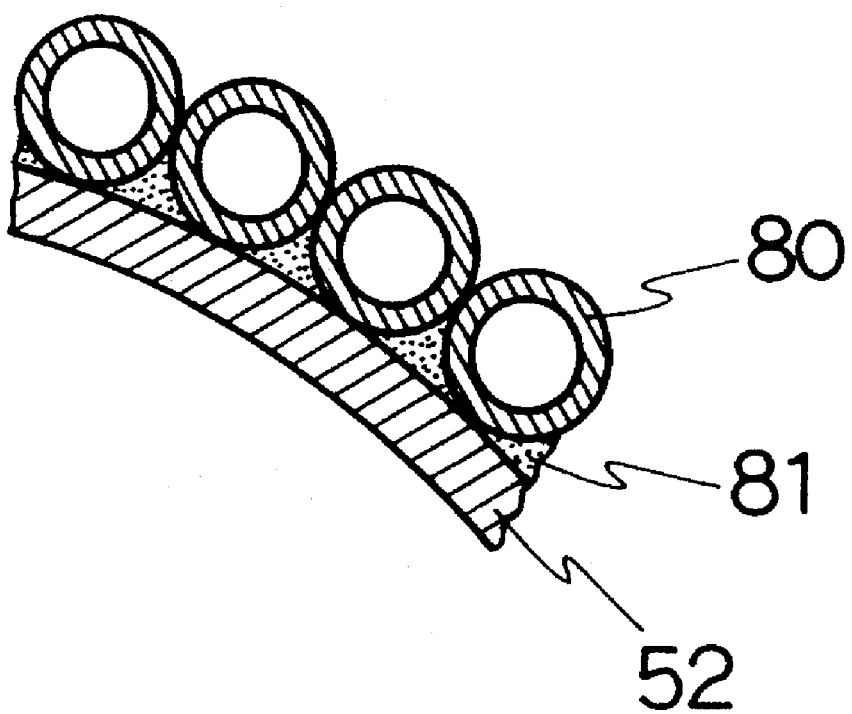
FIG. 15 is a partial sectional view showing relevant part in FIG. 7.

Numeral 80 indicates tubular member which is wound on the spherical surface of the reflector 52 in such a manner as to be closely connected to each other thereon, made of metal pipe having superior heat conductivity such as copper, one side being connected to fine tube 79 and the other to silicone tube 65, thereby introduced out side of casing 57. As shown in FIG. 15, numeral 81 indicates heat conductive filling plugged to space between metal pipe of cooler 80 and reflector 52 which can be used the solidified powder of aluminium with epoxy resin or silicon resin. Numeral 82 indicates heat exchanger disposed to out side of the casing 57, comprising pump 83, metal pipe 84 having excellent heat conductivity which is coiled to a spiral form and fan 85. Pump 83 and metal pipe are connected to tube 65 serially. From fan 85 cool air is blown against metal pipe 84 for the purpose of cooling. Namely, pump 83 makes fluid 54 run out, after passage through transparent cell 91 in the casing 57 via tube 65. Further through cooler 80, then fluid 54 returns to pump 83 tube 65 and metal pipe 84. At transparent cell 91 and cooler 80, the fluid 54 which absorbs infrared light and is heated thereby, is cooled down while passing metal pipe 84.

Figure 16:
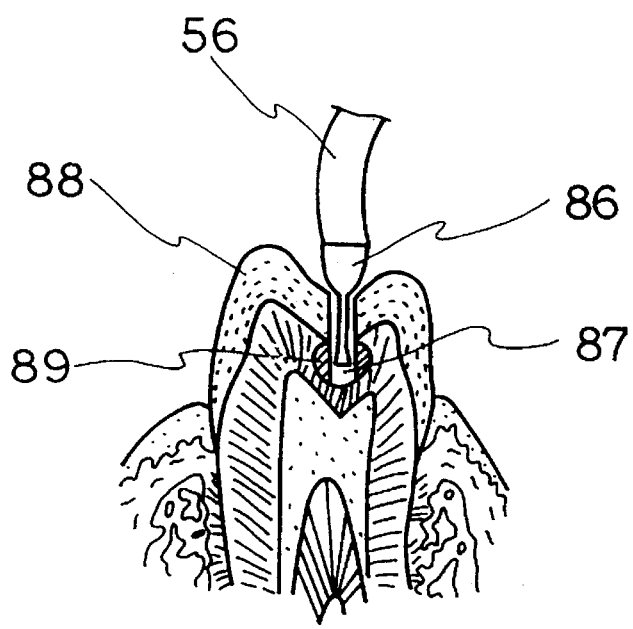
FIG. 16 is a sectional view showing an embodiment of the use of the present invention.
Figure 17:
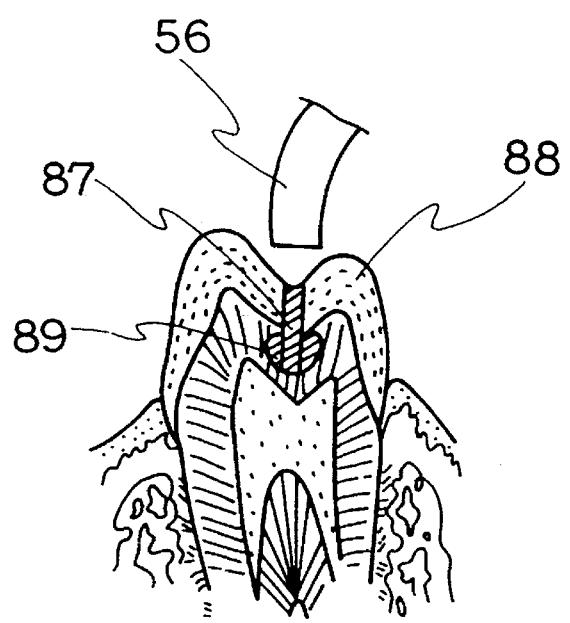
FIG. 17 is a sectional view showing an embodiment of the use of the present invention.

FIGS. 16 and 17 illustrate an embodiment of polymerization and curing of composit resin inlay, herein the tip of light guide 56 is provided with small light guide 86. The tip of small light guide 86 is formed into a triangle shape. The passed light through inside of small light guide 86 is emitted to the outside as it is (shown in FIG. 16 central lower side). Additionally, the light emitted throughout light guide 56, out side of the small light guide 86, impinges to cavity 87 further disperses to the side direction by reflection at the triangle-shaped position. The triangle-shaped portion mentioned above can be of a ball like-shape. After photopolymerizable adhesive is applied to the inner surface of cavity 87 of teeth 88, composite resin inlay field, and said small light guide 86 is inserted, accordingly light is irradiated to composite resin inlay 89 for curing (FIG. 16). Further composit resin inlay 89 is filled into the whole cavity 87, light from light guide 56 is irradiated thereto without small light guide 86. Thus, composite resin inlay 89 can be polymerized and made to cure even if it is carried out in a mouth for cavities 87 with undercut.

In accordance with the present invention, lights emitted from the light source pass through the transparent cell charged with coolant so that the infrared lights are removed from the emitted lights, and the lights incident to the formed article. The about eighty percent of the infrared lights are cut off, for this reason temperature of the formed article hardly rises and photopolymerization resin used for the pattern is cured. The resin which is polymerized and cured is taken out from the polymerization reactor so that the next step is readily performed. For this reason, the efficient work can be realized.

Further, in accordance with the present invention, temperature rise of the formed article is prohibited. For this reason, bad effects on the photopolymerization resin part of the formed article due to the temperature rise such as deformation, boiling of the liquid of monomer or the like is prohibited from generating so that the article having high precision and high strength without bubbles can be obtained.

Furthermore, accordance with the present invention, the cooling efficiency is high. Therefore, the lamp having power higher than that of the conventional one can be used. For this reason, time for polymerization and curing can be shortened so that efficiency of workability can be improved. With respect to the conventional photopolymerization reactor, it takes about three minutes to about four minutes to polymerize, while with respect to the apparatus of the present invention, it can be cured for about 30 to about 40 seconds to cure.

Further, in accordance with the present invention, the transparent cell is integrally formed of heat resistant glass. Therefore, even if heating and cooling are repeated for a long interval in the state as to be equipped near the light source, the coolant is hardly leaked so that durability of the cell can be improved.

According to the present invention, there is provided a small-sized light irradiation device for dental use, wherein the emission light from a light source is transmitted through a cell charged forth fluid for transmitting visible light and because of elimination of infrared light therein and of emission of only visible light through the light guide, the emission light can be heatless, accordingly irradiation against cavities of teeth can be carried out without heating of the effected part. Therefore, the patient can be treated comfortably without pain resulted from heat. Further, according to the invention, there is provided an avoidance of harmful influence against human body by ultraviolet light irradiation, because of the elimination of ultraviolet light by a cell transmissive to visible light make it possible not to irradiate ultraviolet light against tissue in a mouth.

Further, according to the invention, there is provided the possibility to use an emission lamp with higher power than prior ones because of extremely high efficiency of the cooling of light source, therefore making it possible to carry out curing of inlay in a mouth to overcome the difficult insufficiency of the light dose in the prior art, simultaneously to shorten time for polymerization of the photopolymerizable resin and to improve working efficiency. Incidentally, photopolymerizing can be completed in about 30 to 40 sec. by the light irradiator of this invention.

Though several embodiments of the present invention are described above, it is to be understood that the present invention is not limited only to the above-mentioned, various changes and modifications may be made in the invention without departing from the spirit and scope thereof.

What we claim is:

1. A photopolymerization reactor for dental use comprising:

a light source emitting at least visible light and infrared light;

at least one transparent cell charged with a coolant disposed to the emission side of said light source, to absorb infrared light, said transparent cell composed of a disc shaped main body having a hollow space therein which is formed integrally with heat resistant glass;

pipes in communication with a pump, a heat exchanger and said at least one transparent cell for circulation of the coolant, said heat exchanger cooling the coolant which has been heated in the at least one transparent cell; and a board for mounting a formed article which is composed of materials for a pattern made of photopolymerizable resin, impinging the light thereon from said light source after transmitting through said transparent cells.

2. A small-sized light irradiator for dental use comprising:

(a) a light source emitting visible, infrared and ultraviolet light provided with substantially a half ball-shaped reflector which converges at least visible light of said three kinds of light to a predetermined direction;

(b) a transparent cell transmissive to visible light disposed to the emission side of said light source to absorb infrared and ultraviolet light, said transparent cell being connected to a pump and a heat exchanger via a tube;

(c) a light guide to impinge lights passing through said transparent cell from one side end, and emit from the other side end which is directed to a predetermined direction; and (d) a casing with a handle enclosing said light source and transparent cell, provided with said light guide to its one end;

wherein said transparent cell has a hollow space therein charged with fluid, said fluid being circulated by the pump such that fluid heated in said transparent cell is cooled by said heat exchanger.

3. The small-sized light irradiator of claim 2, wherein said transparent cell is composed of disc-like shaped cell main body having a hollow space therein and two fine tubes for fluid circulation fixed to said cell main body to communicate with said hollow space.

4. The small-sized light irradiator of claim 2, wherein said transmission of visible light is composed of conical shaped cell main body having a hollow space therein and two fine tubes for fluid circulation fixed to said cell main body to communicate with said hollow space, wherein said conical shaped cell is disposed such that a bottom portion of said conical shaped cell is faced to the light source, a tip of said conical shaped cell is faced to a side of one of said light guide.

5. The small-sized light irradiator of claim 2, wherein said transparent cell is integrally formed so as to be combined with said reflector, and wherein said reflector has a duplex structure such that a space for communicating with the hollow space within said transparent cell is formed in the reflector.

6. The small-sized light irradiator of claim 2, wherein a part of said tubes are wound so as to be in contact with an outside surface of said reflector, and wherein said tubes are made of such a metal pipe as to have a good heat conductivity capable of absorbing heat of said reflector.

7. The small-sized light irradiator of claim 2, wherein said pump and said heat exchanger are accommodated in said casing.

8. The small-sized light irradiator of claim 2, wherein said pump and said exchanger are arranged in such a manner as to be separated from said casing.

* * * * *